United States Patent [19]

Brock et al.

[11] Patent Number: 5,658,734
[45] Date of Patent: Aug. 19, 1997

[54] PROCESS FOR SYNTHESIZING CHEMICAL COMPOUNDS

[75] Inventors: Phillip Joe Brock, Sunnyvale; William Dinan Hinsberg, Fremont; Jeffrey William Labadie, Sunnyvale; Glenn McGall, Mountain View; Gregory Michael Wallraff, Morgan Hill, all of Calif.

[73] Assignee: International Business Machines Corporation, Armonk, N.Y.

[21] Appl. No.: 544,376

[22] Filed: Oct. 17, 1995

[51] Int. Cl.$^6$ .................... C12Q 1/68; G01N 33/543
[52] U.S. Cl. .................. 435/6; 435/91.1; 435/969; 436/518; 436/809; 436/86; 530/334; 530/335; 530/810; 536/25.3; 536/25.31; 935/88
[58] Field of Search ............... 435/6, 7.92, 7.95, 435/91.1, 969, 973; 436/518, 527, 807, 809, 89, 86; 536/25.3–25.34; 428/426, 532; 935/88; 530/333, 334, 335, 810

[56] References Cited

U.S. PATENT DOCUMENTS 5,143,854   9/1992   Pirrung et al. .

FOREIGN PATENT DOCUMENTS

PCT/US92/
10183   5/1993   WIPO .

OTHER PUBLICATIONS

Maskos et al., "Oligonucleotide hybridisations on glass supports: a novel linker for oligonucleotide synthesis and hybridisation properties of oligonucleotides synthesised in situ". Nucleic Acids Research, vol. 20, No. 7 pp. 1679–1684.

Fodor et al., "Light–Directed, Spatially Addressable Parallel Chemical Synthesis", Research Article, Science, vol. 251, Feb. 15, 1991.

*Primary Examiner*—Paula K. Hutzell
*Assistant Examiner*—Rachel Heather Freed
*Attorney, Agent, or Firm*—Robert B. Martin

[57] ABSTRACT

The present invention relates to a process for synthesizing on a single substrate a plurality of chemical compounds having diverse structures. The process involves the use of a bilayer photoresist to build up selected regions of the array in a step wise fashion.

15 Claims, No Drawings

PROCESS FOR SYNTHESIZING CHEMICAL COMPOUNDS

TECHNICAL FIELD

The present invention relates to a process for synthesizing on a single substrate a plurality of chemical compounds having diverse structures. In particular the present invention relates to a process for synthesizing on a single substrate a plurality of polymers such as polypeptides or polynucleotides having diverse monomer sequence.

BACKGROUND OF THE INVENTION

Synthesis of a plurality of diverse chemical compounds on a single substrate is known in the art. For example Fodor et al., U.S. Pat. No. 5,445,934 (incorporated herein by reference for all purposes) discloses forming an array by the steps of (i) disposing on a substrate a layer of linker molecules having photoremovable protecting groups; (ii) imagewise exposing the layer to radiation to activate selected regions; (iii) attaching a monomer with photoremovable protecting group to the activated regions and repeating the steps of activation and attachment until a plurality of polymer of the desired length and sequence are synthesized. The method of Fodor et al. has been used to form dense arrays of biological molecules of, for example, oligonucleotides, and is considered pioneering in the industry. The arrays formed according to the methods disclosed in Fodor et al. may be used, for example, in drug discovery, oligonucleotide sequencing, oligonucleotide sequence checking, and other applications.

While Fodor's above technique has met with substantial success, it would be desirable to provide additional and improved techniques for forming arrays of biological materials.

Other objects and advantages will become apparent from the following disclosure.

SUMMARY OF THE INVENTION

The present invention relates to a process for synthesizing an array comprising a plurality of chemical compounds having diverse structures such as a diverse monomer sequences on a substrate. The first step involves coating a layer of protective polymer onto a layer of foundational molecules which are immobilized on a substrate. The foundational molecules have a labile protecting group on a chemically reactive site. A layer of polymeric, radiation-sensitive photoresist is coated onto the layer of protective polymer. The photoresist layer is exposed to radiation and then developed using one or more solvents to imagewise uncover selected regions of the layer of foundational molecules. The uncovered portions of the layer of foundational molecules are treated to remove the protecting group and activate the molecules. Preferably, the remaining portion of photoresist and protective polymer layers are then stripped off. The last step involves bonding a chemical molecule preferably having a labile protecting group onto an uncovered reactive site of the foundational molecules. The process steps may then be repeated uncovering other regions of the substrate and reacting the activated layer with other chemical molecules to form the array. The process is conveniently used to make polypeptides and oligo/polynucleotides preferably comprising a few monomers up to about 50 monomers.

A more thorough disclosure of the present invention is presented in the detailed description which follows.

DETAILED DESCRIPTION OF THE INVENTION

The present invention relates to a process for synthesizing on a single substrate a plurality of chemical compounds, preferably biochemical compounds having diverse monomer sequence.

As used herein, these terms will have the following meaning: "Oligonucleotide" is a nucleic acid sequence composed of two or more nucleotides. An oligonucleotide can be derived from natural sources but is often synthesized chemically. It is of any size. An "oligonucleotide analogue" refers to a polymer with two or more monomeric subunits, wherein the subunits have some structural features in common with a naturally occurring oligonucleotide which allow it to hybridize with a naturally occurring oligonucleotide in solution. For instance, structural groups are optimally added to the ribose or base of a nucleoside for incorporation into an oligonucleotide, such as a methyl or allyl group at the 2-O position on the ribose, or a fluoro group which substitutes for the 2'-O group, or a bromo group on the ribonucleoside base. The phosphodiester linkage, or "sugar-phosphate backbone" of the oligonucleotide analogue can also be substituted or modified, for instance with methyl phosphates or O-methyl phosphates. Another example of an oligonucleotide analogue for purposes of this disclosure includes "peptide nucleic acids" in which a polyamide backbone is attached to oligonucleotide bases, or modified oligonucleotide bases. Oligonucleotide analogues optionally comprise a mixture of naturally occurring nucleotides and nucleotide analogues.

A "nucleoside" is a pentose glycoside in which the aglycone is a heterocyclic base; upon the addition of a phosphate group the compound becomes a nucleotide. The major biological nucleosides are β-glycoside derivative of D-ribose or D-2-deoxyribose. Nucleotides are phosphate esters of nucleosides which are generally acidic in solution due to the hydroxy groups on the phosphate. The nucleosides of DNA and RNA are connected together via phosphate units attached to the 3' position of one pentose and the 5' position of the next pentose. Nucleotide analogues and/or nucleoside analogues are molecules with structural similarities to the naturally occurring nucleotides or nucleosides as discussed above in the context of oligonucleotide analogues. "Biochemical compound" is a compound in living organisms, an oligonucleotide or an oligonucleotide analogue.

Suitable substrates for use in the process of the present invention include silicon dioxide, borosilicate glass, organic polymers and other solid substrates known to those skilled in the art which have a surface bearing reactive sites suitable for immobilizing a layer of molecules having a labile protecting group.

Preferably, the substrate is first coated with an initial layer of linker molecules. Suitable linker molecules for glass substrates include molecules which have (i) functionality that provides attachment to the surface of the substrate (e.g. an alkoxysilane group), and (ii) functionality that provides a reactive site suitable for bonding to another molecule (e.g. a hydroxy group). Suitable linker molecules are disclosed by Fodor et. al., the disclosure of which is incorporated herein by reference above.

According to one embodiment of the invention herein, the first step of the process of the present invention involves coating a layer of developable protective polymer onto a layer of foundational molecules which is attached to the substrate preferably through the linker molecules. The foundational molecules have labile protecting groups which shield chemically reactive sites on the foundational molecules. Initially, the foundational layer of molecules is attached directly to the substrate preferably through a layer of linker molecules. Subsequently in the process, the foundational molecules are intermediate structures comprising a plurality of molecules. Suitable protective polymers for use in the process include soluble polyimides and poly (vinylalcohol) (PVA). The polymer is dissolved in a suitable coating solvent such as anisole, water (for PVA), N-methyl pyrrolidone or N,N-dimethylacetamide.

The protective polymer can be coated on the layer of foundational molecules using art-known techniques such as spin or spray coating, or doctor blading. Preferably, the polymer layer is then heated to an elevated temperature of about 70° to 150° C. for a short period of time of about one to ten minutes to remove the casting solvent. The layer suitably has thickness of about one-half microns.

In the next step of the process, a polymeric, radiation sensitive resist is coated onto the layer of protective polymer in a manner similar to step 1. Preferred resists are crosslinking negative resists which are resistant to the organic solvents utilized to transfer the lithographic pattern from the resist through the protective polymer. Suitable crosslinking resists include crosslinking epoxy resists, cyclized rubber resists such as KTFR, and polyvinylcinnamate resists, such as KPR (KPR and KTFR are commercial resists materials known to those skilled in the art.) Other negative resists are disclosed in W. DeForest, "Photoresist Materials and Processes", McGraw-Hill, New York, 1975. Suitable casting solvents for the uncrosslinked resists include cyclohexanone and xylene. Other photoresists suitable for use in the process of the present invention will be known to those skilled in the art such as those described in W. Moreau, "Semiconductor Lithography", Plenum Press, New York, 1988 which is incorporated herein by reference. The resist layer is also preferably heated to an elevated temperature of about 60° to 100° C. for a short period of time of about one to ten minutes. The resist layer suitably has a thickness of about one-half to 5 microns.

In the next step of the process, the resist layer is imagewise exposed to radiation, suitably electromagnetic radiation such as ultraviolet, preferably at a wavelength of about 200–550 nm. The preferred radiation source is mercury or mercury-xenon lamp. Preferably, for large-scale manufacturing, the imaging dose is less than 200 mj/cm$^2$ to enhance throughput of the arrays.

The next step in the process involves development of the latent image in the resist with a suitable developer solvent. Suitable developer solvents for exposed crosslinked resists include: the solvent used for initial coating; xylene or mixtures of xylene with other solvents for cyclized rubber resists; xylene and cyclohexanone for polyvinylcinnamate resists; and cyclohexanone for epoxy resists. A suitable developer solvent for polyimide is anisole or the solvent used for initial coating. The image is developed through the resist layer and then further developed (transferred) through the layer of protective polymer to the underlying layer of foundational molecules with one or more suitable solvents. The development step results in the uncovering of selected portions of the underlying layer of foundational molecules. Depending on the solubility properties of the protective polymer layer and the resist layer, the development step can be carried out as a single operation using a single developing solvent, or as two sequential operations each utilizing a different developing solvent.

In the next step of the process, the uncovered portions of the underlying layer of foundational molecules are treated to activate the foundational molecule by removal of the protecting group to form a reactive bonding site on the molecule. Preferably, the uncovered portions of the layer of foundational molecules are contacted with a solution to cleave the protective group from the molecule. Suitable protective groups include acid-labile groups such as the triphenylmethyl (trityl) and substituted trityl groups e.g. dimethoxytrityl (DMT), the t-butexycarbonyloxy (TBOC) group, acetals and ketals, and labile esters; base-labile groups such as the 9-fluorenylmethoxycarbonyl (FMOC) group; and other labile groups such as allyloxycarbonyl group removeable with palladium catalysts. Suitable cleaving solutions include solutions of strong acids (for acid-labile groups), and solutions of ammonia, amines or other strong bases for base-labile groups. A wide range of labile protecting groups are known to those skilled in the art such as disclosed in T. Greene, "Protective Groups in Organic Synthesis," Wiley, New York, 1981, the disclosure of which is incorporated herein by reference. A suitable active bonding site on the foundational molecules is a hydroxy substituent (R-OH) reactive to phosphoramidite coupling reagent. Another suitable active bonding site is the primary amino group, as used in polypeptide synthesis. Other functionality could also be useful such as ketones and aldehydes which can be protected and deprotected for coupling reactions.

Preferably, the remaining portions of resist and protective polymer layer are then stripped off. Suitable stripping solutions for exposed crosslinking resists with polyimide protective layer include dichloromethane, N-methylpyrrolidone and acetone.

The next step of the process involves bonding chemical structural units, such as monomers, preferably having a labile protecting group, to the activated layer of foundational molecules. Preferably, the process of the present invention is utilized to synthesize biochemical polymers. As used herein monomer shall include dimers, trimers and oligomers. Suitable monomers include L and D amino adds, nucleotides, monosaccharides, peptoids and synthetic nucleotide analogs in protected and activated forms. Preferred monomers include the following nucleotides: adenosine phosphate; guanosine phosphate; cytidine phosphate, uridine phosphate, deoxyadenosine phospate, deoxyguanosine phosphate, deoxycytidine phosphate and deoxythymidine phosphate in protected and activated forms, as well as mimetics thereof. The protective and activating groups used depend on specifics of the synthetic chemistry being used and are well known to those skilled in the art. The monomer nucleotides are preferably bonded to the activated layer of molecules through 3'→5' phosphodiester bonds. The protecting group is preferably bonded at the 5' site. Other suitable chemical structural units for bonding to the foundational molecules and process for bonding is disclosed in Fodor et al., Science, 251, p. 767 (1991), the disclosure of which is incorporated herein by reference.

The process may be repeated until the desired number of chemical molecules having diverse structural sequence are formed on the substrate.

After completion of the synthesis of the desired number of chemical molecules on the array, the protecting groups on the molecules are preferably removed.

The process of the present invention also relates screening biochemical polymers e.g. oligonucleotides for determination of binding affinity using the arrays made by the process of the present invention. For example, fluorescent labeled unknown biochemical polymers or oligomers can be structurally identified by their binding affinities on the array using art known techniques. In such screening activities, the substrate containing the sequences is exposed to an unlabeled or labeled receptor such as an oligonucleotide or any one of a variety of other receptors. In one preferred embodiment the polymers are exposed to a first, unlabeled receptor of interest and, thereafter exposed to a labeled receptor-specific recognition element, which is, for example, an antibody. This process will provide signal amplification in the detection stage.

The receptor molecules may bind with one or more polymers on the substrate. The presence of the labeled receptor and, therefore, the presence of a sequence which binds with the receptor is detected in a preferred embodiment through the use of autoradiography, detection of fluorescence with a charge-coupled device, fluorescence microscopy, or the like. The sequence of the polymer at the locations where the receptor binding is detected may be used to determine all or part of a sequence which is complementary to the receptor.

The following examples are detailed descriptions of process of the present invention. The detailed preparations fall within the scope of, and serve to exemplify, the more generally described process set forth above. The examples are presented for illustrative purposes only, and are not intended as a restriction on the scope of the invention.

EXAMPLE 1

Glass substrates bearing 5'-dimethoxytrityl (DMT) protected phosphoramidite-activated nucleotide foundation molecules were overcoated with a 0.5 μm thick layer of Ciba-Geigy XU218, a commercial polyimide, by spin coating from a 7 weight percent solution in anisole. The substrates were contact baked on a hotplate at 100° C. for 60 seconds to remove solvent from the film. The substrate was then spin coated with a nominal 1 μm film of photoresist and baked for 60 seconds at 100° C. The photoresist composition was comprised of a solution of 16.2 grams of epoxy resin, 1.0 gram triphenylsulfonium hexafluoroantimonate, and 1.0 gram 9-anthracenemethanol in 83.8 grams of cyclohexanone. The bilayer coated wafer was exposed through a mask on a contact aligner with a dose of 54 mj/cm$^2$ with a 365 nm bandpass filter in place. The exposed wafer was baked at 100° C. for 60 seconds, quenched on a cold plate, then spray developed on a photoresist spinner with cyclohexanone for 15 seconds at 1500 rpm. The polyimide barrier layer was wet etched on a photoresist spinner by first puddling anisole for 7 seconds, then spinning off the anisole at 1500 rpm and quenching by rinsing with cyclohexanone. The patterned substrates were treated with a 5% solution of dichloroacetic acid in cyclohexanone (v/v) for 10 minutes to remove the DMT from the nucleotide selectively in the exposed regions of the substrate and form reactive hydroxyl groups. No detectable degradation in the bilayer pattern fidelity was observable by visual inspection. The resist was stripped by soaking the plate in methylene chloride for 3 minutes and rinsing with methylene chloride. The substrate was then derivatized with a Fluoreprime(™) fluorescein phosphoromidite and tetrazole in acetonitrile, using an Applied Biosystems Inc (ABI) DNA synthesizer. This step functionalizes the free hydroxyl reactive groups with a fluorescent moiety in order to determine the fidelity of the patterning process. After treatment of the Fluoreprimed samples with an ethylene diamine/ethanol mixture, the fluorescent output of the surface of the substrate was measured with a laser array scanner to determine the regions where the fluorescent phosphoramidite moiety coupled to the reactive hydroxyl group. A pattern resolution of 8 micron lines and spaces was achieved.

EXAMPLE 2

| Abbreviations | |
|---|---|
| A | 2'-Deoxyadenosine |
| T | Thymidine |
| G | 2'-Deoxyguanosine |
| C | 2'-Deoxycytidine |
| DNA | Deoxyribonucleic acid |
| DCA | Dichloroacetic acid |

Following the procedure of Example 1, the process of the present invention was used to mask four distinct 3 mm diameter sites on a substrate to which was attached a DMT protected foundational molecule. The unmasked area of the substrate was detritylated with 20% DCA/cylohexanone and capped with acetate groups using acetic anhydride/pyridine reagent. On the uncapped sites, a DMT-terminated CATC oligomer was synthesized on the ABI DNA synthesizer. The bilayer process was used to mask 3 of the 4 sites and deposit A on the unmasked site. This operation was repeated in turn with G, C, and T, addressing the other three areas. The sample was then subjected to further synthesis using conventional DNA synthetic processes to couple TAGAAC to all 4 areas. The resultant sample had areas of four distinct undecamers with the structure CATCXTAGAAC, X=A,G, C, or T. A fluorescent labeled target incorporating a sequence complementary to CATCGTAGAAC was contacted with the sample. The fluorescent plot of the sample after hydridization showed the expected high fluorescence intensity at the site where X=G and low intensity at the other three sites where there was a mismatch with the target at the fifth monomer from the surface. This result demonstrates the fidelity of the oligomer prepared using the method of the invention.

Although this invention has been described with respect to specific embodiments, the details thereof are not to be construed as limitations for it will be apparent that various embodiments, changes, and modifications may be resorted to without departing from the spirit and scope thereof, and it is understood that such equivalent embodiments are intended to be included within the scope of this invention.

We claim:

1. A process for synthesizing a plurality of chemical compounds having diverse structure on a substrate comprising the steps of:
   (a) coating a layer of protective polymer onto a layer of first molecules which are disposed on a substrate and have a labile protecting group;
   (b) coating a layer of radiation sensitive resist onto the layer of protective polymer;
   (c) imagewise exposing the resist layer to radiation;
   (d) developing the image to imagewise expose a portion of the layer of first molecules;
   (e) treating the exposed portion of the layer of first molecules to remove the protecting group; and
   (g) bonding second molecules to the exposed first molecules.

2. The process of claim 1 wherein the resist is a crosslinking negative resist.

3. The process of claim 2 wherein the resist is an epoxy resist.

4. The process of claim 2 wherein the protective polymer is polyimide or poly(vinyl alcohol).

5. A process for synthesizing a plurality of biochemical compounds having diverse structure on a substrate comprising the steps of:

(a) coating a layer of protective polymer onto a layer of first molecules which are disposed on a substrate and have a labile protecting group;

(b) coating a layer of radiation sensitive resist onto the layer of protective polymer;

(c) imagewise exposing the resist layer to radiation;

(d) developing the image to imagewise expose a portion of the layer of first molecules;

(e) treating the exposed portion of the layer of first molecules to remove the protecting group; and (g) bonding second molecules to the exposed first molecules.

6. The process of claim 5 wherein the polymeric resist is a crosslinking negative resist.

7. The process of claim 6 wherein the resist is an epoxy resist.

8. The process of claim 6 wherein the protective polymer is polyimide or poly(vinyl alcohol).

9. The process of claim 7 wherein the protective polymer is a polyimide.

10. The process of claim 5 wherein the layer of first molecules is a layer of nucleoside or nucleotide molecules.

11. The process of claim 5 wherein the second layer molecules are a layer of phosphoramidite nucleotide molecules.

12. The process of claim 11 wherein the nucleotide molecules are protected with dimethoxy trityl substituent.

13. The process of claim 11 wherein the nucleotide molecule is adenosine phosphate, guanosine phosphate, cytidine phosphate, uridine phosphate, deoxyadenosine phosphate, deoxyguanosine phosphate, deoxycytidine phosphate or deoxythymidine phosphate.

14. The process of claim 13 wherein the protecting group is triphenylmethyl, dimethoxy triphenylmethyl, t-butoxycarbonyloxy or fluorenylmethoxycarbonyl.

15. A process for screening unknown biochemical polymer for binding affinity comprising the steps of (a) exposing an array to biochemical polymers, the array comprising a plurality of biochemical compounds having diverse structure bonded to a substrate and made by the process of;

(i) coating a layer of protective polymer onto a layer of first molecules which are disposed on a substrate and have a labile protecting group;

(ii) coating a layer of radiation sensitive resist onto the layer of protective polymer;

(iii) imagewise exposing the resist layer to radiation;

(iv) developing the image to imagewise expose a portion of the layer of first molecules;

(v) treating the exposed portion of the layer of first molecules to remove the protecting group; and (vi) bonding second molecules to the exposed first molecules; and (b) detecting on the array the locations of binding of the biochemical polymer to the biochemical compounds.

* * * * *

UNITED STATES PATENT AND TRADEMARK OFFICE
CERTIFICATE OF CORRECTION

PATENT NO.         : 5,658,734
APPLICATION NO. : 08/544376
DATED              : August 19, 1997
INVENTOR(S)       : Phillip J. Brock et al.

It is certified that error appears in the above-identified patent and that said Letters Patent is hereby corrected as shown below:

On the Title Page
Item [73] Assignee: International Business Machines Corporation, Armonk, NY should read Assignees: International Business Machines Corporation, Armonk, NY and Affymetrix, Inc., Santa Clara, CA Signed and Sealed this Twenty-seventh Day of October, 2009

David J. Kappos
*Director of the United States Patent and Trademark Office*